United States Patent [19]
Yamaura

[11] Patent Number: 5,595,176
[45] Date of Patent: Jan. 21, 1997

[54] PULSE OXIMETER

[75] Inventor: Masahiko Yamaura, Tokyo, Japan

[73] Assignee: Nihon Kohden Corporation, Tokyo, Japan

[21] Appl. No.: 351,533

[22] Filed: Dec. 7, 1994

[30] Foreign Application Priority Data

Dec. 7, 1993 [JP] Japan .................................. 5-306281

[51] Int. Cl.⁶ .................................................. A61B 5/00
[52] U.S. Cl. .......................................... 128/633; 356/41
[58] Field of Search ................................ 128/633, 664, 128/665, 666; 356/41

[56] References Cited

U.S. PATENT DOCUMENTS

| 5,188,108 | 2/1993 | Secker | 128/633 |
| 5,285,783 | 2/1994 | Secker | 128/633 |
| 5,285,784 | 2/1994 | Secker | 128/633 |

Primary Examiner—Angela D. Sykes
Assistant Examiner—Eric F. Winakur
Attorney, Agent, or Firm—Sughrue, Mion, Zinn, Macpeak & Seas

[57] ABSTRACT

A pulse oximeter includes light-emitting devices for irradiating different wavelengths of light into a living tissue through which arterial blood flow, a light-receiving device for detecting at least one of transmitted and reflected light after the different wavelengths of light have been absorbed by the living tissue, first correlation function computing device for determining first correlation function for the waveform of received light at one of the different wavelengths obtained from the output of the light-receiving device, second correlation function computing device for determining second correlation function for the waveforms of received light at another of the different waveforms obtained from the output of the light-receiving device, dividing device for determining the ratio between the first correlation function obtained by the first auto-correlation function computing device and the second correlation function obtained by the cross-correlation function computing device, the ratio determined on the basis of appropriate values of the two correlation functions, and computing device for calculating the oxygen saturation of the arterial blood on the basis of the output of the dividing device.

4 Claims, 5 Drawing Sheets

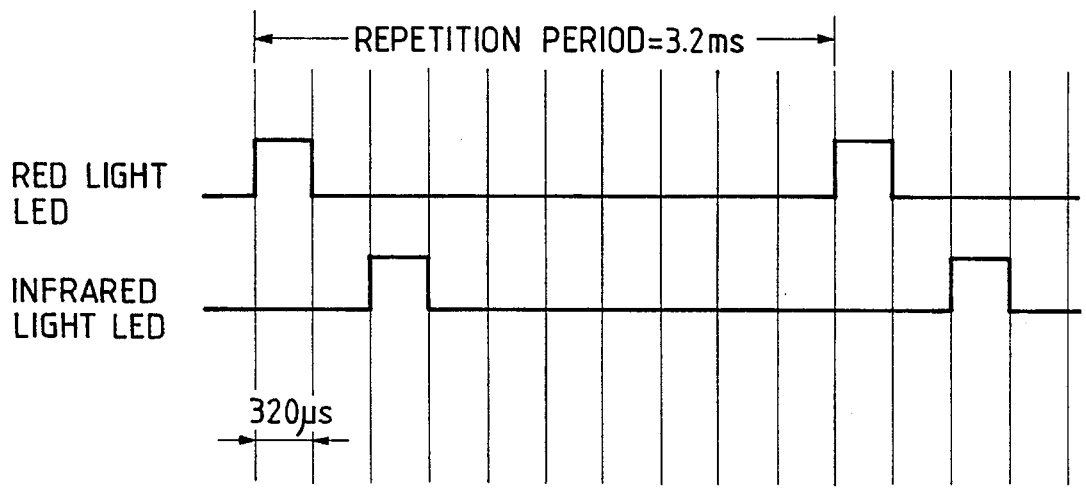

PULSE OXIMETER

BACKGROUND OF THE INVENTION

1. Field of the invention

This invention relates to a pulse oximeter with which the oxygen saturation of arterial blood flowing through the body of an object can be measured continuously in a non-invasive manner using the principle that light of two different wavelengths, say, red light and infrared light, have different light absorbent characteristics in the object.

2. Related Art

Pulse oximeters are conventionally used to determine the oxygen saturation of arterial blood in a non-invasive manner. The operating principle of the pulse oximeter is as follows: at least two wavelengths of light (typically, red light and infrared light) that have different transmission characteristics for oxyhemoglobin and deoxyhemoglobin are launched into a fingertip or earlobe, and the light that has been transmitted through or reflected from the living tissue is received, and the arterial oxygen saturation is calculated on the basis of the fact that the light absorbency of blood differs at the respective wavelengths of interest depending upon the oxygen saturation.

The waveforms of the received light contain pulsating components due to variations in blood flow with the pulse rate of the object. The pulsating waveforms that are obtained for two or more wavelengths of light are ideally similar in shape and the only difference is in amplitude on account of the difference in light absorbency.

If the reception waveform (after logarithmic process) that is obtained with the light of one wavelength is written as $x(t)$, the reception waveform (after logarithmic process) that is obtained with the light of the other wavelength is written as $y(t)$, $x(t)$ and $y(t)$ which are similar in shape can be related by:

$$x(t)=K \cdot y(t)$$

where K is the proportionality constant. Thus, the oxygen saturation ($SpO_2$) of arterial blood has ideally one-to-one correspondence to the proportionality constant K, FIG. 5 is a block diagram of a conventional pulse oximeter that operates on the above-described principle of measurement. As shown, a LED drive circuit 1 is connected to two light-emitting diodes (LED) 2 and 3 that constitute light-emitting devices; typically, one LED 2 is for emitting red light at a wavelength of 660 nm and the other LED 3 is for emitting infrared light at a wavelength of 940 nm. Since the LED drive circuit 1 is under the control of a timing generator circuit 9, the LEDs 2 and 3 emit red and infrared light alternately at a repetition period as shown in FIG. 6, which light are then launched into a living tissue 4 through which arterial blood flows. The two wavelengths of light that are transmitted through or reflected from the living tissue 4 are received by a photodiode 5 working as a light-receiving device and thence enter a current voltage converter circuit (I-V converter circuit) 6 so that they are converted to voltage signals. The waveforms of signal leaving the I-V converter circuit 6 are passed through a bandpass filter (BPF) 7, thence to a demodulator 8. In response to a timing signal from the timing generator circuit 9, the reception waveform of red light is distributed to a logarithmic amplifier (log AMP) 10 whereas the reception waveform of infrared light is sent to another logarithmic amplifier (log AMP) 11.

After logarithmic processing in the amplifiers 10 and 11, the reception waveforms $x(t)$ and $y(t)$ for red and infrared light, respectively, are isolated into a waveform buffer 25, with $x(t)$ being also fed to a peak-bottom detector 26. In the peak-bottom detector 26, both peaks and bottoms of the input waveform $x(t)$ are detected and time-related sequence information of peaks and bottoms is sent to the waveform buffer 25. On the basis of his time-related sequence information, maximum displacements $\Delta x$ and $\Delta y$ per heart beat are determined for the input waveforms $x(t)$ and $y(t)$, respectively, and the signals for $\Delta x$ and $\Delta y$ are sent to a divider 27.

In the divider 27, constant K ($=\Delta x/\Delta y$) which has one-to-one correspondence to the oxygen saturation is calculated and the thus determined K is sent to the next computing stage 28, where the oxygen saturation S is determined by $S=n(K)$. The thus calculated oxygen saturation S is displayed on a display 29.

The logarithmic amplifiers 10 and 11, waveform buffer 25, peak-bottom detector 26, divider 27 and computing stage 28 can be configured in a microcomputer, so that signals from the demodulator 8 are converted to a digital form by means of an A/D converter before they are fed into the microcomputer for the necessary processing.

As described above, constant $K=\Delta x/\Delta y$ ideally has one-to-one correspondence to the oxygen saturation. In fact, however, the reception waveforms $x(t)$ and $y(t)$ are variable with an unexpected factor due to the influence of such effects as the site and method of sensor attachment. Stated more specifically, the pulsating waveform in each reception waveform should ideally consist of the pulsating component of arterial blood but, in fact, external effects such as the displacement of the attached sensor, body movements and incoming light will introduce irregular noise (artifacts) other than the pulsation component.

If such irregular noise is involved in the process of calculating the oxygen saturation using the amplitude information of reception waveforms $x(t)$ and $y(t)$, the calculated value will naturally have low reliability.

Therefore, for precise measurement of the arterial oxygen saturation using a pulse oximeter, it is critical to provide for positive elimination of the erratic occurrence of irregular noise.

SUMMARY OF THE INVENTION

The present invention has been proposed under these circumstances and has as the principal object providing a pulse oximeter that is capable of positive elimination of the irregular noise due to body movements and other undesired effects, thereby assuring precise measurement of the arterial oxygen saturation.

According to an aspect of the present invention, there is provided a pulse oximeter comprising:

light-emitting devices for launching different wavelengths of light into a living tissue through which arterial blood flows;

a light-receiving device for detecting either transmitted or reflected light that occurs after said different wavelengths of light have been absorbed by the living tissue;

auto-correlation function computing means for determining an auto-correlation function for the waveform of received light at one of said different wavelengths as obtained from the output of said light-receiving device;

cross-correlation function computing means for determining a cross-correlation function for the waveforms of received light at said different waveforms as obtained from the output of said light-receiving device;

dividing means for determining the ratio between the auto-correlation function as obtained by said auto-correlation function computing means and the cross-correlation function as obtained by said cross-correlation function computing means, said ratio being determined from appropriate values of said two correlation functions; and computing means for calculating the oxygen saturation of the arterial blood on the basis of the output of said dividing means.

According to another aspect of the present invention, there is provided that a pulse oximeter comprising:

light-emitting devices for launching different wavelengths of light into a living tissue through which arterial blood flows;

a light-receiving device for detecting either transmitted or reflected light that occurs after said different wavelengths of light have been absorbed by the living tissue;

first auto-correlation function computing means for determining an auto-correlation function for the waveform of received light at one of said different wavelengths as obtained from the output of said light-receiving device;

second auto-correlation function computing means for determining an auto-correlation function for the waveform of received light at the other of said different wavelengths as obtained from the output of said light-receiving device;

dividing means for determining the ratio between the auto-correlation functions as obtained by said first and second auto-correlation function computing means, said ratio being determined from appropriate values of said two correlation functions; and computing means for calculating the oxygen saturation of the arterial blood on the basis of the output of said dividing means.

According to the present invention, the pulse oximeter of the invention is so adapted that after launching different wavelengths of light into a living tissue through which arterial blood flows, the light either transmitted through or reflected from the tissue is received and that an auto-correlation function and a cross-correlation function are determined for the waveforms of the received light, followed by computing the oxygen saturation of arterial blood on the basis of the ratio of appropriate values of those correlation functions. Because of this arrangement, the irregular noise due to artifacts such as body movements and incoming noise can be effectively eliminated to permit precise and reliable measurement of the oxygen saturation.

BRIEF DESCRIPTION OF THE DRAWINGS

FIG. 6 is a chart showing the timed relationship between two light-emitting diodes in emitting different wavelengths of light to be launched into a living tissue.

DETAILED DESCRIPTION OF THE PREFERRED EMBODIMENTS

Figure 1:
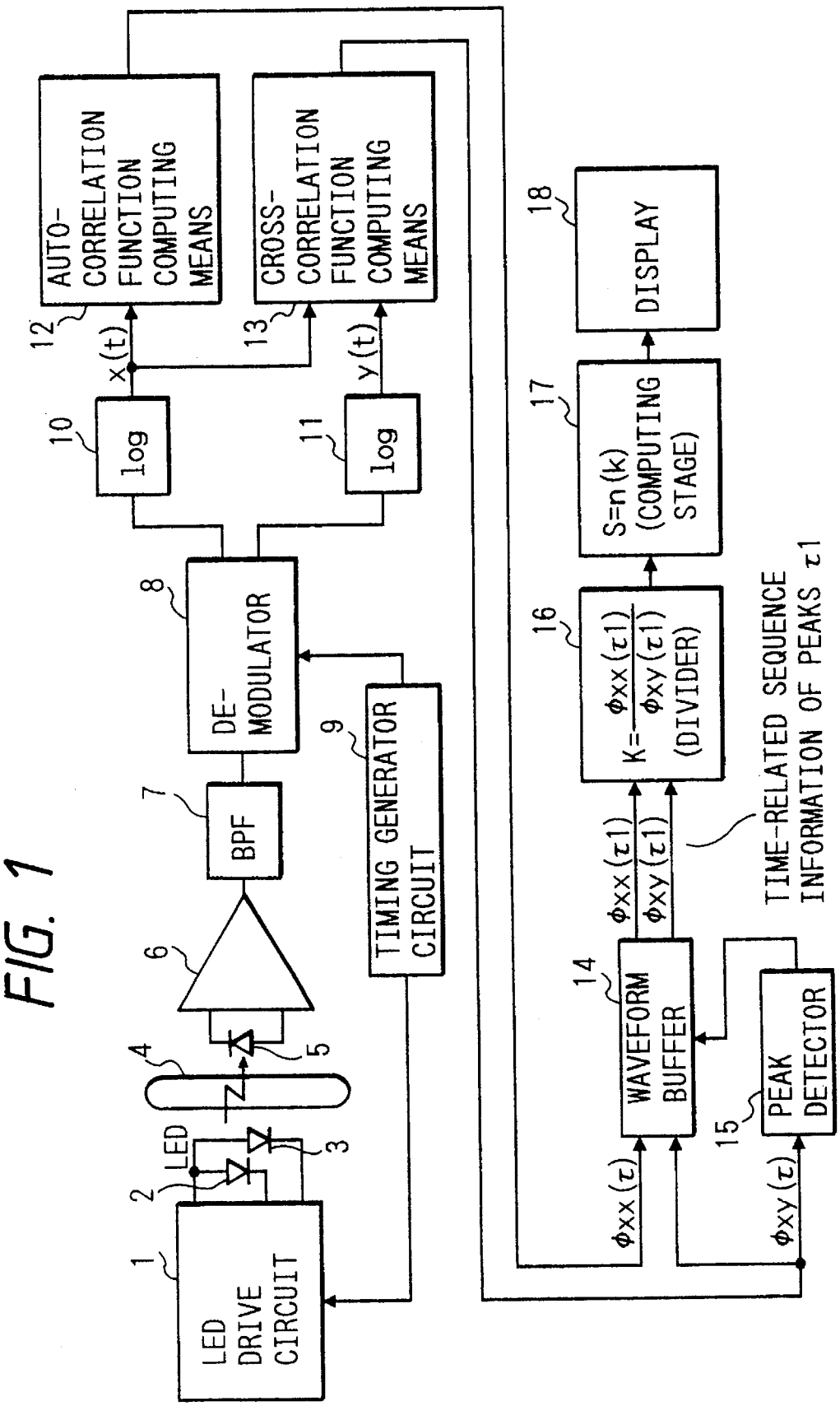
FIG. 1 is a block diagram showing a pulse oximeter according to an embodiment of the invention.

The operating principle of the invention will now be described.

It is first noted that the pulsating waveform contains frequency information that is dependent on heart rate. In a simple method, the heart rate may be determined by setting a trigger level for the pulsating waveform output but this has the potential to produce unstable values of heart rate owing to the irregular noise. Under the circumstances, an auto-correlation function may be used to eliminate the irregular noise and thereby determine the correct heart rate. As a matter of fact, fetal monitors (which receive sound signal rather than the light signal received by the pulse oximeter) apply an auto-correlation function to ultrasonic Doppler signals derived from heart beats to thereby determine an instantaneous heart rate.

In the next step, the similarity of the two resulting waveforms $x(t)$ and $y(t)$ is utilized to determine a cross-correlation function for the two waveforms in the same manner as adopted to determine the auto-correlation function. If the two waveforms $x(t)$ and $y(t)$ are similar to each other, differing only in terms of amplitude, the waveform of the thus determined cross-correlation function is also similar to the auto-correlation function and the difference in amplitude is expressed by the same ratio as with the original waveforms.

The auto-correlation function and the cross-correlation function are each the result of extracting only the heart beat derived frequency component of the input waveform $x(t)$ or $y(t)$ and hence is essentially free from the erratic irregular noise. Therefore, by determining the amplitude ratio between the auto-correlation function and the cross-correlation function, the arterial oxygen saturation can be calculated without being influenced by the irregular noise.

The theory of the invention will be described below in greater detail. As already mentioned, two kinds of reception waveform $x(t)$ and $y(t)$ which result when two different wavelengths of light (i.e., red light and infrared light) are launched into a living tissue through which arterial blood flows are similar in shape and can be related by the defining equation:

$$x(t)=K \cdot y(t) \quad (1)$$

However, considering the possibility that the reception waveforms $x(t)$ and $y(t)$ occasionally contain the irregular noise, it is not justified in relating the proportionality constant K to the oxygen saturation by one-to-one correspondence.

For the purposes of the invention, let the reception waveform $x(t)$ be divided into $s(t)$ which is the frequency component derived from heart beat and $f(t)$ which is the irregular noise component derived from artifacts, and also let the reception waveform $y(t)$ be similarly divided into $1/K \cdot s(t)$ (frequency component) and $f'(t)$ (irregular noise component). Thus, $x(t)$ and $y(t)$ are redefined as follows:

$$x(t)=s(t)+f(t) \quad (2)$$

$$y(t)=1/K \cdot s(t)+f'(t) \quad (3)$$

Auto-correlation function $\phi_{xx}(\tau)$ of waveform $x(t)$ and cross-correlation function $\phi_{xy}(\tau)$ of two waveforms $x(t)$ and $y(t)$ are defined as follows:

$$\phi_{xx}(\tau) = \lim_{T \to \infty} \frac{1}{T} \int_0^\infty x(t)x(t+\tau)dt \quad (4)$$

$$\phi_{xy}(\tau) = \lim_{T \to \infty} \frac{1}{T} \int_0^\infty x(t)y(t+\tau)dt \quad (5)$$

The auto-correlation function of the waveform of a certain time function is determined by the procedure of multiplying said waveform by itself with the phase shifted successively, summing up the multiplication products and averaging the sum. If the phase shift is varied, the resulting average will vary accordingly and if the waveform of interest contains a certain frequency component, a value close to the average for zero-phase shift is obtained when the variation in phase shift is equal to the periodic interval of that waveform. This means a high degree of correlation between two waveforms at the points that are offset in phase by that amount. Thus, analysis of phase-related waveforms provides waveforms that have peaks at each periodic interval of the periodic function that is contained in the original waveforms and one can extract any periodic component that is contained in the seemingly irregular waveform of interest.

Alternatively, the area of overlap between two waveforms of the same shape may be considered; suppose here that the waveform of interest is expressed by a perfect periodic function; if such waveforms are successively placed in an overlapping relationship, the area of overlap will decrease progressively with the increasing phase shift as compared to the area of overlap that occurs when there is no phase shift at all. If the phase shift is further increased to approach the cycle of the relevant periodic function the area of overlap starts to increase and the two waveforms will completely overlap again when the phase shift becomes equal to the cycle. Therefore, by extracting the areas of successive overlaps in association with the respective amounts of phase shift, one can obtain a periodic function that agrees with the period of the original waveforms. The same discussion will apply to the cross-correlation functions of waveforms x(t) and y(t).

Having thus defined the auto-correlation function $\phi_{xx}(\tau)$ and the cross-correlation function $\phi_{xy}(\tau)$, we may substitute eqs. (2) and (3) into eqs. (4) and (5), so that $\phi_{xx}(\tau)$ and $\phi_{xy}(\tau)$ can be rewritten as follows:

$$\phi_{xx}(\tau) = \phi_{ss}(\tau) + \phi_{ff}(\tau) \quad (6)$$

$$\phi_{xy}(\tau) = 1/K \cdot \phi_{ss}(\tau) + \phi_{ff'}(\tau) \quad (7)$$

Figure 4:
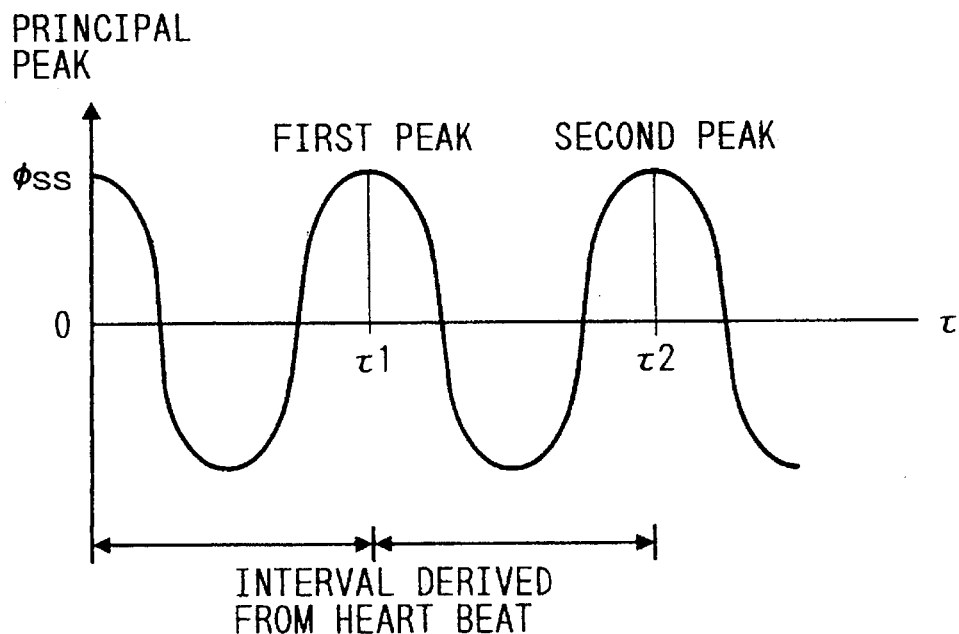
FIG. 4 is a diagram showing the waveform of an auto-correlation function for the periodic function portion of an input waveform.

Since s(t) is a periodic function, the auto-correlation function $\phi_{ss}(\tau)$ for s(t) is also a periodic function as characterized in FIG. 4. On the other hand, f(t) and f'(t) represent irregular noise having no periodicity; therefore, the auto-correlation function $\phi_{ff}(\tau)$ for f(t) and the cross-correlation function $\phi_{ff'}(\tau)$ for f(t) and f'(t) are each a delta ($\delta$) function.

Therefore, looking at the area of overlap between waveforms, $\phi_{ff}(\tau)$ and $\phi_{ff'}(\tau)$ each have a definite value at a point where there is no phase shift ($\tau=0$) since two waveforms overlap completely; however, if there is a phase shift, the area of overlap decreases considerably and approaches sufficiently near zero with averaging over infinite time. Further, considering the nature of $\phi_{ff}(\tau)$ and $\phi_{ff'}(\tau)$ as irregular noise, no two waveforms will completely overlap again no matter how large the phase shift will be and either, function cannot have a definite value except in the state where there is no phase shift at all. Thus, $\phi_{ff}(\tau)$ and $\phi_{ff'}(\tau)$ are characterized as $\delta$ function and amplitude exists only at the origin of $\tau$. Hence, eqs. (6) and (7) can be rewritten by the following approximations:

$$\phi_{xx}(\tau) = \phi_{ss}(\tau) \quad (8)$$

$$\phi_{xy}(\tau) = 1/K \cdot \phi_{ss}(\tau) \quad (9)$$

Rearranging eqs. (8) and (9), we get $$K = \phi_{xx}(\tau)/\phi_{xy}(\tau) \quad (10)$$

Eq. (10) tells the ratio of the auto-correlation function of the input waveform x(t) over the cross-correlation function of two input waveforms x(t) and y(t). By thusly determining this ratio, we can compute the oxygen saturation of arterial blood with high precision. In addition, since the peak values of the waveforms x(t) and y(t) depend upon the pulsating heart beat of the patient, the period of the waveform of the correlation function $\phi_{ss}(\tau)$ can be used to determine the pulse of the pulse rate of the patient. In fact, the pulse rate determined by the pulse oximeter is as accurate as a pulse rate determined by a fetal monitor.

The precision of calculation of K is affected by which point on the $\tau$ axis is selected. Theoretically, the same value of K should be obtained at all points on the $\tau$ axis but, from a practical viewpoint, calculations are desirably performed at peaks on the $\tau$ axis in order to attain more precise values of K. The principal peak lying at the origin of $\tau(=0)$ is the easiest peak to detect (see FIG. 4). However, as mentioned in the preceding paragraph, the irregular noise is expressed by $\delta$ function and, hence, noise-derived amplitude will be superposed on the periodic function at points in the neighborhood of the origin of $\tau$. Hence, the value of K can be determined with the highest precision by performing the necessary calculations after detecting the primary peak at $\tau=\tau 1$.

The present invention also permits the oxygen saturation to be computed on the basis of the auto-correlation functions of the respective reception waveforms x(t) and y(t). The operating principle of measurement by this approach will now be described.

The auto-correlation function $\phi_{xx}(\tau)$ of waveform x(t) and the auto-correlation function $\phi_{yy}(\tau)$ of waveform y(t) are respectively defined as follows:

$$\phi_{xx}(\tau) = \phi_{ss}(\tau) + \phi_{ff}(\tau) \quad (11)$$

$$\phi_{yy}(\tau) = 1/K^2 \cdot \phi_{ss}(\tau) + \phi_{f'f'}(\tau) \quad (12)$$

For the same reason as set forth above, $\phi_{ff}(\tau)$ which is the auto-correlation function of f(t) and $\phi_{f'f'}(\tau)$ which is the auto-correlation function of f'(t) can each be regarded as $\delta$ function and, hence, eqs. (11) and (12) can be rewritten by the following approximations:

$$\phi_{xx}(\tau) = \phi_{ss}(\tau) \quad (13)$$

$$\phi_{yy}(\tau) = 1/K^2 \cdot \phi_{ss}(\tau) \quad (14)$$

Rearranging eqs. (13) and (14), we get $$K^2 = \phi_{xx}(\tau)/\phi_{yy}(\tau) \quad (15)$$

Since K has one-to-one correspondence to the oxygen saturation and takes only positive values, $K^2$ of course has one-to-one correspondence to the oxygen saturation. Therefore, by determining the ratio between the auto-correlation functions of the respective input waveforms x(t) and y(t), one can compute the oxygen saturation of arterial blood with high precision.

Preferred embodiments of the invention will now be described in detail with reference of accompanying drawings. In the following description, those parts which are the same as in the prior art are identified by like numerals to simplify the explanation of overlapping portions.

Figure 5:
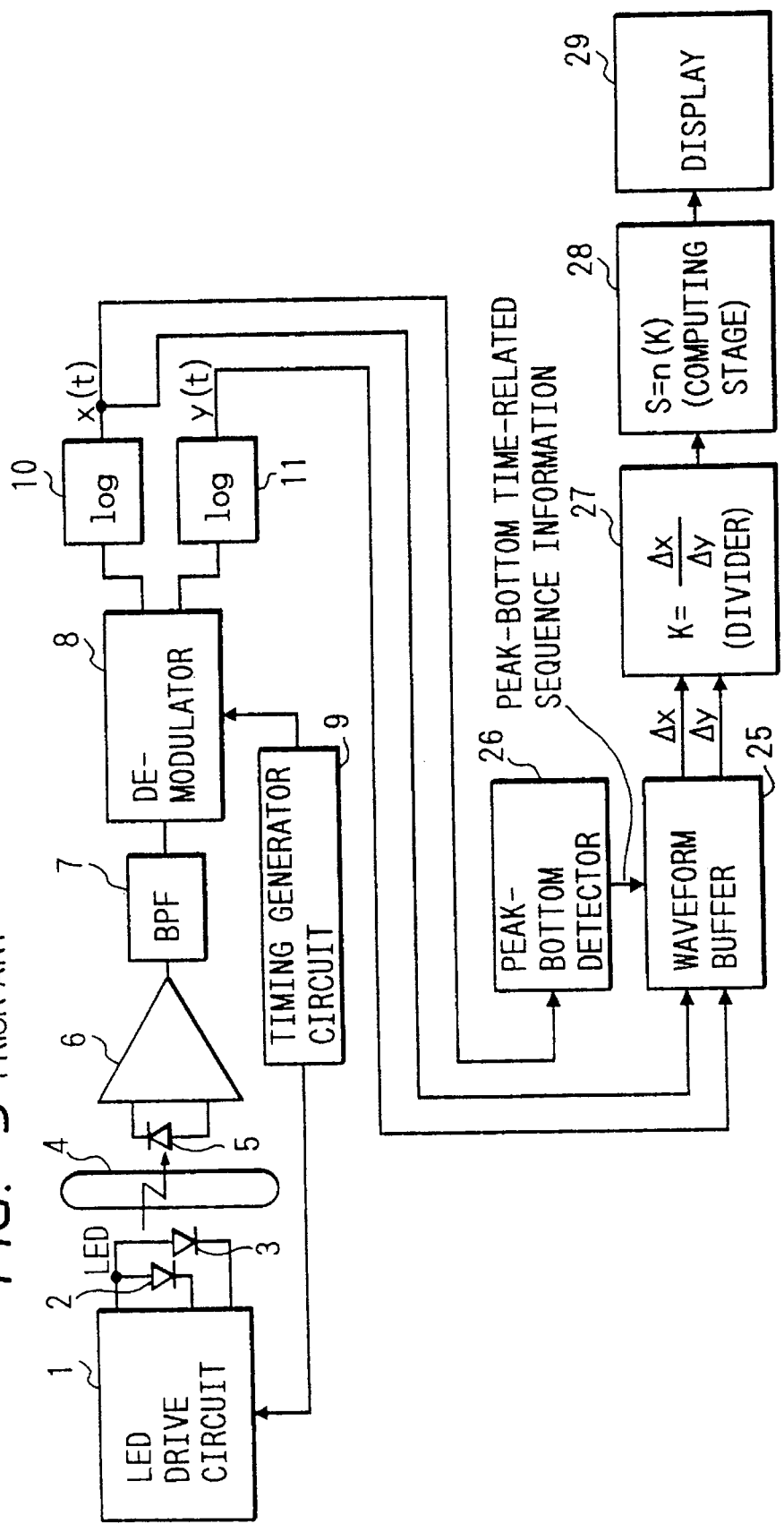
FIG. 5 is a block diagram showing a prior art pulse oximeter.

FIG. 1 is a block diagram showing a pulse oximeter according to an embodiment of the invention. As already described with reference to FIG. 5, demodulator 8 separates the received signal to light of two different wavelengths in response to a timing signal from timing generator circuit 9 and the two reception waveforms, one for red light and the other for infrared light, are sent to logarithmic amplifiers 10 and 11 for logarithmic processing. The reception waveform of red light x(t) is sent to both auto-correlation function computing means 12 and cross-correlation function computing means 13, whereas the reception waveform of infrared light y(t) is sent to cross-correlation function computing means 13.

The auto-correlation function computing means 12 determines the auto-correlation function $\phi_{xx}(\tau)$ of input waveform x(t), which is then sent to waveform buffer 14. The cross-correlation function computing means 13 determines the cross-correlation function $\phi_{xy}(\tau)$ of input waveforms x(t) and y(t), which is sent to both waveform buffer 14 and peak detector 15.

The peak detector 15 detects the time-related sequence information of peaks ($\tau=\tau1$) which is the phase information corresponding to the primary peak of cross-correlation function $\phi_{xy}(\tau)$ and this information is sent to the waveform buffer 14. The provision of peak detector 15 enables precise measurement of pulse rate on the basis of the detected information of peaks.

The waveform buffer 14 determines the values of correlation functions at the phase point $\tau1$ in the time-related sequence information of peaks from the correlation function waveform (correlogram). The thus determined functional values $\phi_{xx}(\tau1)$ and $\phi_{xy}(\tau1)$ are sent to divider 16.

The divider 16 receives the input functional values $\phi_{xx}(\tau1)$ and $\phi_{xy}(\tau1)$ and calculates K as follows:

$K=\phi_{xx}(\tau1)/\phi_{xy}(\tau1)$

The thus determined constant K is sent to the next computing stage 17, which calculates the oxygen saturation S by:

$S=n(K)$

The determined S is displayed on display 18.

In the embodiment under consideration, the oxygen saturation is determined by peak detection because peak values provide a greater amplitude for the waveforms of correlation functions and thereby assure higher precision in calculation of the oxygen saturation. The invention can of course be embodied without performing peak detection since the value of K is theoretically constant even if the phase $\tau$ is determined other than at peaks.

It should also be noted that the logarithmic amplifiers 10 and 11, auto-correlation function computing means 12, cross-correlation function computing means 13, waveform buffer 14, peak detector 15, divider 16 and computing stage 17 may be configured in a microcomputer, so that signals from the demodulator 8 are converted to a digital form by means of an A/D converter before they are fed into the microprocessor for the necessary processing.

Figure 2:
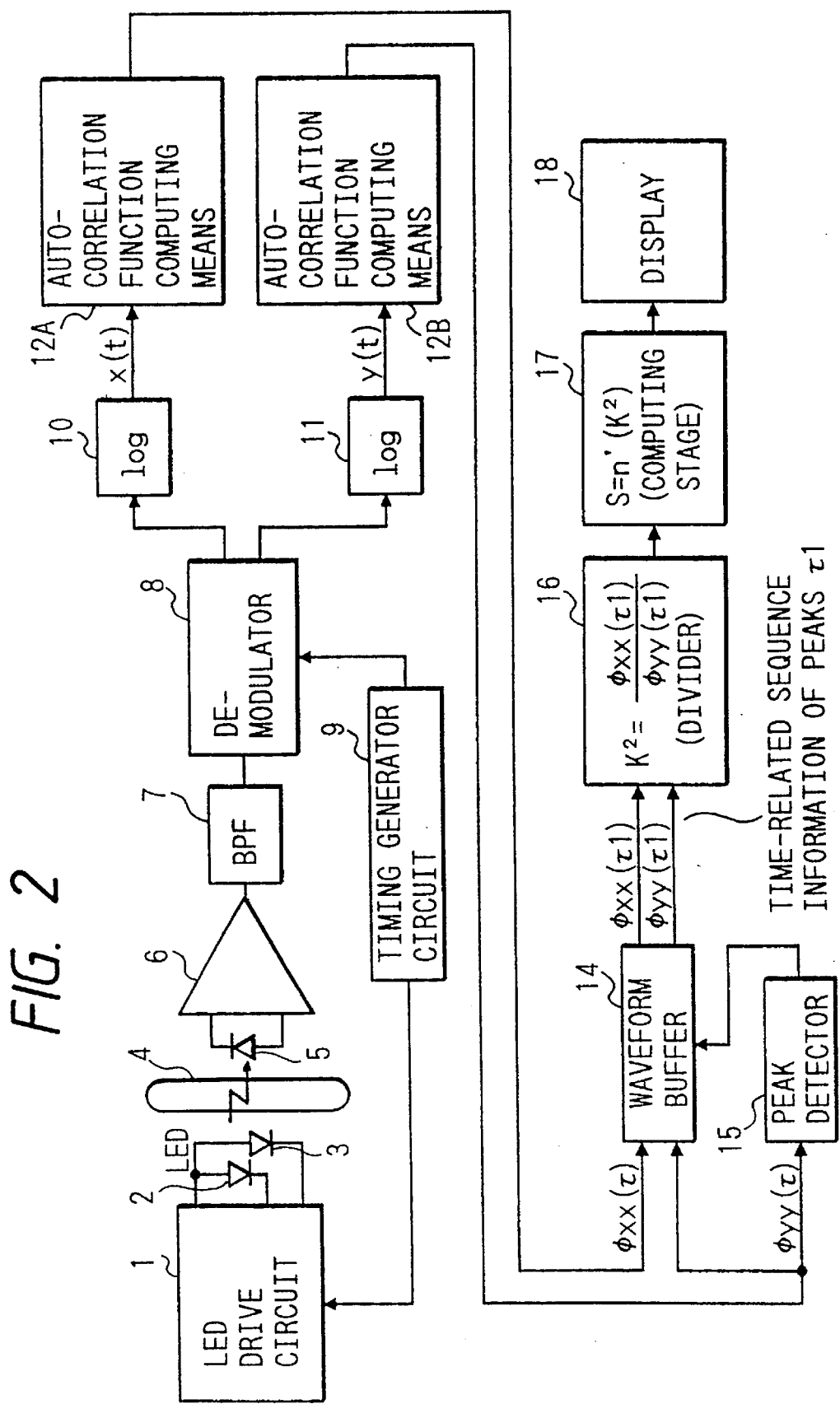
FIG. 2 a block diagram showing a pulse oximeter according to another embodiment of the invention.

FIG. 2 shows a pulse oximeter according to another embodiment of the invention. In this embodiment, the reception waveform of red light x(t) emerging from the demodulator 8 is sent to first auto-correlation function computing means 12A whereas the reception waveform of infrared light y(t) also emerging from the demodulator 8 is sent to second auto-correlation function computing means 12B.

The auto-correlation function computing means 12A and 12B determine the auto-correlation functions $\phi_{xx}(\tau)$ and $\phi_{yy}(\tau)$ of the input waveforms x(t) and y(t), respectively, and these auto-correlation functions are isolated into waveform buffer 14, with function $\phi_{yy}(\tau)$ being also fed to peak detector 15.

The peak detector 15 detects the time-related sequence information of peaks $\tau1$ corresponding to the primary peak of auto-correlation function $\phi_{yy}(\tau)$ and this is sent to waveform buffer 14.

The waveform buffer 14 determines the values of correlation functions at the phase point $\tau1$ in the time-related sequence information of peaks ($\tau1$) and the thus determined functional values $\phi_{xx}(\tau1)$ and $\phi_{yy}(\tau1)$ are sent to divider 16.

The divider 16 receives the input functional values $\phi_{xx}(\tau1)$ and $\phi_{yy}(\tau1)$ and calculates $K^2$ as follows:

$K^2=\phi_{xx}(\tau1)/\phi_{yy}(\tau1)$

The thus determined constant $K^2$ is sent to the next computing stage 17, which calculates the oxygen concentration S by:

$S=n'(K^2)$

The determined S is displayed on display 18.

Figure 3:
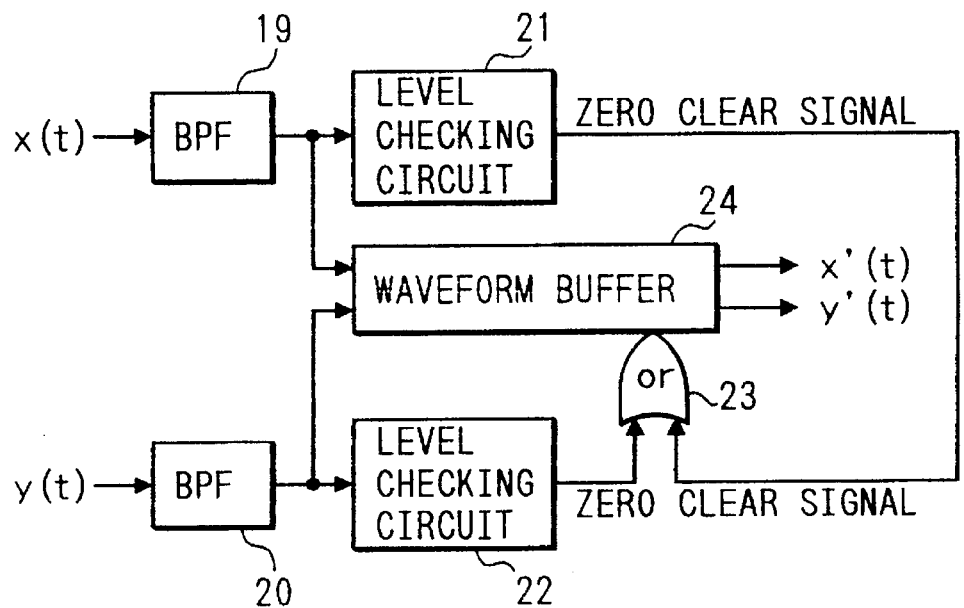
FIG. 3 is a block diagram showing the essential part of a pulse oximeter according to yet another embodiment of the invention.

FIG. 3 shows the essential part of a pulse oximeter according to still another embodiment of the invention. The portion shown in FIG. 3 is to be connected between demodulator 8 and each of auto-correlation function computing means 12 and cross-correlation function computing means 13 in the circuit shown in FIG. 1, or between demodulator 8 and each of the auto-correlation function computing means 12A and 12B in the circuit shown in FIG. 2.

Referring to FIG. 3, reception waveforms x(t) and y(t) coming as separate entities from demodulator 8 are passed through bandpass filters (BPF) 19 and 20, respectively; x(t) is thereafter sent to a level checking circuit 21 and a waveform buffer 24 whereas y(t) is sent to another level checking circuit 22 and the same waveform buffer 24. The bandpass filters 19 and 20 may be of a common type with fixed characteristics; however, higher reliability in measurements can be imparted by using adaptive filters the characteristics of which are optimized according to a specific frequency.

Level checking circuits 21 and 22 provide for constant comparison with the previous peak value and if the input level exceeds an n multiple (n is variable with the situation) of the previous peak value, each circuit supplies a ZERO CLEAR signal to waveform buffer 24 via an OR gate 23 so that the content of the buffer is cleared.

This level checking feature ensures that any extremely large change that occurs to input is regarded as noise due to a body movement so that no input signals will be supplied to correlation function computing means 12/13 or 12A/12B. Basically, the invention provides for elimination of the adverse effects of artifacts such as body movements by computing correlation functions, but the waveforms of correlation functions can potentially be deformed for a very short period the moment the waveform of an artifact enters the system and even such transient effects can be eliminated by performing a remedial process using the circuit shown in FIG. 3.

As described on the foregoing pages, the pulse oximeter of the invention is so adapted that after launching different wavelengths of light into a living tissue through which arterial blood flows, the light either transmitted through or reflected from the tissue is received and that an auto-correlation function and a cross-correlation function are determined for the waveforms of the received light, followed by computing the oxygen saturation of arterial blood on the basis of the ratio of appropriate values of those correlation functions. Because of this arrangement, the irregular noise due to artifacts such as body movements and incoming noise can be effectively eliminated to permit precise and reliable measurement of the oxygen saturation.

What is claimed is:

1. A pulse oximeter, comprising:

light-emitting devices for irradiating different wavelengths of light into a living tissue through which arterial blood flows, wherein any portion of said different wavelengths of light which pass through said living tissue is considered transmitted light and any portion of said different wavelengths of light which reflect off of said living tissue is considered reflected light;

a light-receiving device for detecting received light, wherein said received light comprises at least one of said transmitted light and said reflected light;

first correlation function computing means for determining a first correlation function for a first waveform of said received light having one of the different wavelengths detected by the light-receiving device;

second correlation function computing means for determining a second correlation function for a second waveform of said received light having another of the different wavelengths detected by the light-receiving device;

dividing means for determining a ratio between the first correlation function obtained by the first correlation function computing means and the second correlation function obtained by the second correlation function computing means, wherein the ratio is determined according to said first and second correlation functions; and computing means for calculating oxygen saturation of the arterial blood on the basis of an output of the dividing means, wherein the first correlation function computing means includes an auto-correlation function computing means and the second correlation function computing means includes a cross-correlation function computing means, wherein said first correlation function is an auto-correlation function, wherein said auto-correlation function is based on said first waveform and a phase shifted version of said first waveform, wherein said second correlation function is a cross-correlation function, and wherein said cross-correlation function is based on said first waveform and a phase shifted version of said second waveform.

2. A pulse oximeter, comprising:

light-emitting devices for irradiating different wavelengths of light into a living tissue through which arterial blood flows, wherein any portion of said different wavelengths of light which pass through said living tissue is considered transmitted light and any portion of said different wavelengths of light which reflect off of said living tissue is considered reflected light;

a light-receiving device for detecting received light, wherein said received light comprises at least one of said transmitted light and said reflected light;

first correlation function computing means for determining a first correlation function for a first waveform of said received light having one of the different wavelengths detected by the light-receiving device;

second correlation function computing means for determining a second correlation function for a second waveform of said received light having another of the different wavelengths detected by the light-receiving device;

dividing means for determining a ratio between the first correlation function obtained by the first correlation function computing means and the second correlation function obtained by the second correlation function computing means, wherein the ratio is determined according to said first and second correlation functions; and computing means for calculating oxygen saturation of the arterial blood on the basis of an output of the dividing means, wherein the first correlation function computing means includes an auto-correlation function computing means and the second correlation function computing means includes an auto-correlation function computing means, wherein said first correlation function is a first auto-correlation function, wherein said first auto-correlation function is based on said first waveform and a phase shifted version of said first waveform, wherein said second correlation function is a second auto-correlation function, and wherein said second auto-correlation function is based on said second waveform and a phase shifted version of said second waveform.

3. A pulse oximeter as claimed in claim 1, wherein said auto-correlation function is a function of a phase difference between said first waveform and said phase shifted version of said first waveform and wherein said cross-correlation function is a function of a phase difference between said first waveform said phase shifted version of said second waveform.

4. A pulse oximeter as claimed in claim 3, wherein said first auto-correlation function is a function of a phase difference between said first waveform and said phase shifted version of said first waveform and wherein said second auto-correlation function is a function of a phase difference between said second waveform and said phase shifted version of said second waveform.

* * * * *